United States Patent [19]

Boyd

[11] Patent Number: 5,146,933

[45] Date of Patent: Sep. 15, 1992

[54] IMPLANTABLE PROSTHETIC DEVICE AND TETHERED INFLATION VALVE FOR VOLUME

[75] Inventor: Lawrence M. Boyd, Memphis, Tenn.

[73] Assignee: Dow Corning Wright Corporation, Arlington, Tenn.

[21] Appl. No.: 764,560

[22] Filed: Sep. 20, 1991

[51] Int. Cl.$^5$ ............................................. A61B 19/00
[52] U.S. Cl. ...................................... 128/899; 623/8; 623/11; 623/901
[58] Field of Search .................... 623/7, 8, 11, 901; 128/899, 898

[56] References Cited

U.S. PATENT DOCUMENTS

| | | | |
|---|---|---|---|
| 3,845,384 | 10/1974 | Stoutenberg et al. | 324/41 |
| 4,222,374 | 9/1980 | Sampson et al. | 128/1 R |
| 4,433,440 | 2/1984 | Cohen | 623/8 |
| 4,467,125 | 8/1984 | Chapp et al. | 568/936 |
| 4,531,244 | 7/1985 | Hamas | 623/8 |
| 4,643,733 | 2/1987 | Becker | 623/8 |
| 4,651,717 | 3/1987 | Jakubczak | 623/8 X |
| 4,773,908 | 9/1988 | Becker | 623/8 |
| 4,841,992 | 6/1989 | Sasaki | 623/8 X |
| 4,944,749 | 7/1990 | Becker | 623/8 |
| 4,955,907 | 9/1990 | Ledergerber | 623/11 X |
| 4,955,909 | 9/1990 | Ersek et al. | 623/11 |
| 4,960,425 | 10/1990 | Yan et al. | 623/8 |
| 4,965,430 | 10/1990 | Curtis et al. | 219/121.69 |
| 5,002,572 | 3/1991 | Picha | 623/11 |

OTHER PUBLICATIONS

"Ion-Beam Microtexturing of Biomaterials", *Medical Device & Diagnostic Industry*, vol. 6, No. 4, Apr., 1984 623-8.

Surgical Technique, "Tissue Expansion-Guidelines Case Analysis", by Gordon H. Sasaki, M.D., 1985, Published by Dow Corning Wright Corporation, Arlington, Tenn. .

Pending U.S. patent application Ser. No. 402,745 filed Sep. 4, 1989, Inventor: James M. Curtis re: Method of Manufacturing an Implantable Article Provided with a Micropillared Surface.

*Primary Examiner*—Ronald Frinks
*Attorney, Agent, or Firm*—John L. Chiatalas

[57] ABSTRACT

According to the invention, there is provided an implantable prosthetic device inflatable by a self-contained resealable valve in combination with an external locator for determining the position of the valve. The prosthesis includes a flexible outer envelope defining a closed lumen and having a valve attached to an area of the envelope with indicia on the valve responsive to the external locator for determining the position of the valve. A plurality of spaced sensors are each fixedly arrayed on the locator so that when the sensors are in a certain non-juxtaposed relationship with the indicia the sensors orientate with one another, signifying a true location of the valve. A multi-compartmental design having a tethered valve for selective inflation of an inner lumen is also disclosed. The tissue-contacting surface of the outer envelope is micro-textured to minimize tissue capsule contracture.

2 Claims, 5 Drawing Sheets

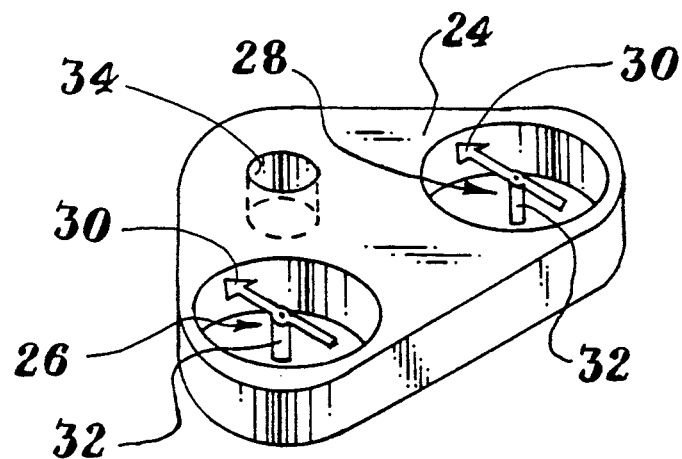
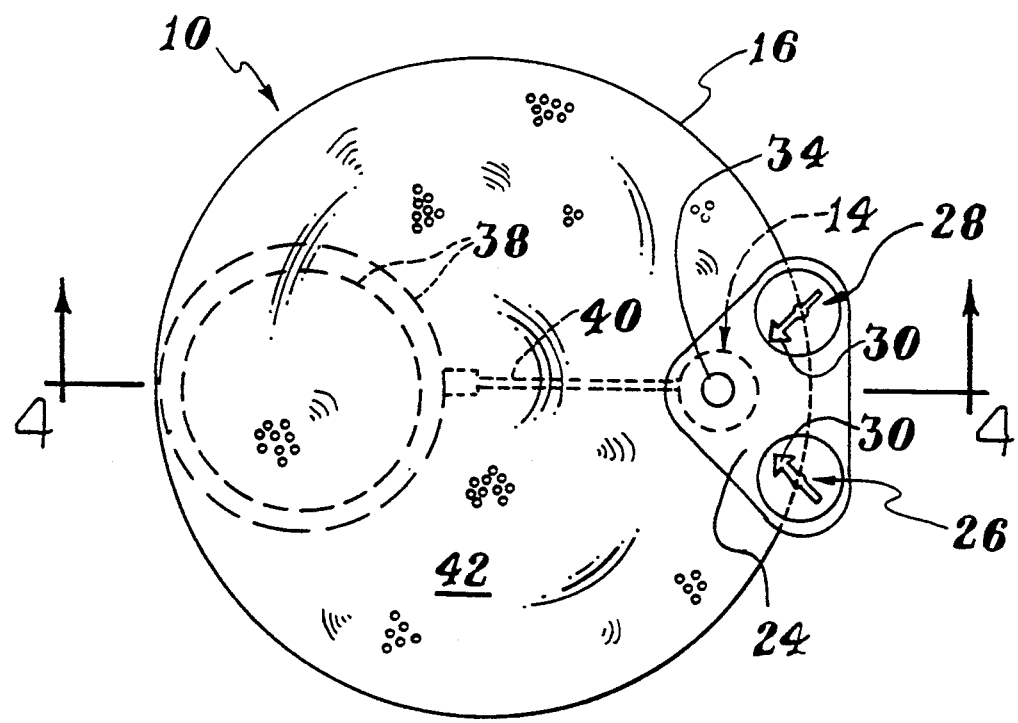

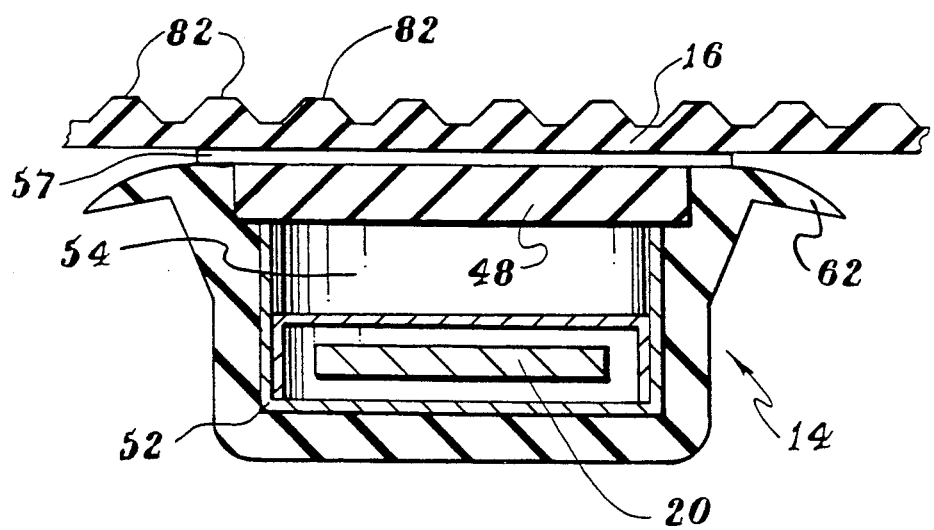
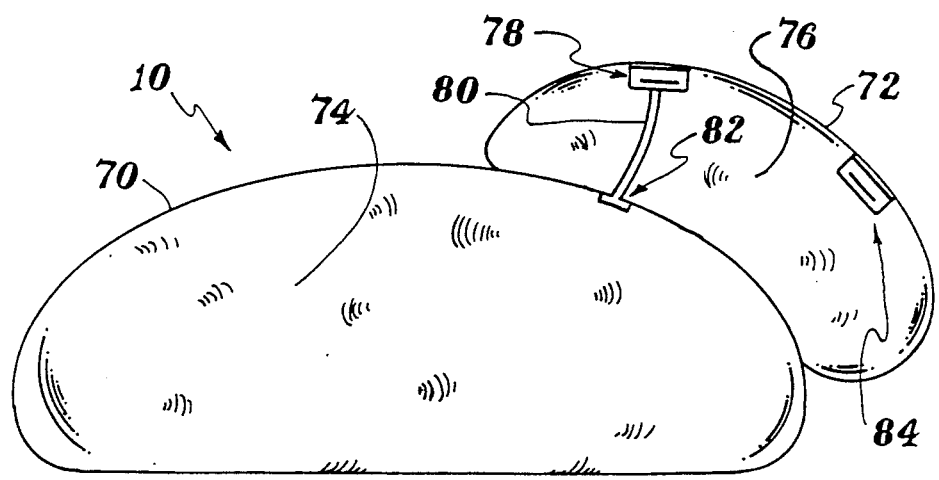

IMPLANTABLE PROSTHETIC DEVICE AND TETHERED INFLATION VALVE FOR VOLUME

BACKGROUND OF THE INVENTION

1. Field of the Invention

This invention relates to prostheses which are inflatable after implantation by means of resealable valves, and particularly to configurations of such valves.

2. Description of the Prior Art

During plastic and reconstructive surgery, it is often necessary to implant an inflatable prosthesis as a means of expanding the tissue and skin in a localized area of the body. This can be done either with a short term or "long-dwelling tissue expander device". Both types of devices require that progressive injections of volume-expanding fluid be made by the physician through a self-sealing valve during successive postoperative outpatient procedures. This is preferably done by percutaneous injection of a silicone gel, saline or other fluid through the valve into a reservoir to fill the lumen of the prosthesis; however, it is often difficult to locate the injection valve among the surrounding tissue. Various means have been employed to determine the location of such valves, including manual palpation, as well as external magnetic devices which sense the position of magnetic material within the valve.

An example of a magnetic locator which is used to find the injection reservoir in a mammary prosthesis is shown in U.S. Pat. No. 4,467,125; however, the device is principally concerned with providing a reinforcing member surrounding the juncture of the valve and outer envelope, intended to prevent the envelope from folding over upon itself during implantation. A similar product is currently sold under the name "MAGNA-SITE", by McGhan Medical Corp. of Santa Barbara, Calif. The magnetic locator device sold with this product resembles a simple stud finder like those used in the carpentry trade, e.g., that shown in U.S. Pat. No. 3,845,384.

U.S. Pat. No. 4,222,374 discloses an external locating device having a magnetic sensor which determines the position of an implanted metallic cardiac infusion pump by direct juxtaposition of the sensor with the ferro-magnetic element. However, there is no reference of such a device being used to locate an inflatable prosthesis, particularly a mammary implant.

Another concern with inflatable prostheses is the formation of a tissue capsule surrounding the implant, which has been known to contract around and, in some patients, significantly compress the implant, causing a great deal of discomfort. Thickness of the tissue which forms the capsule has been found to be an important factor in the incidence of problems related to capsule contracture, which is a complication requiring the physician to either surgically or manually rupture the capsule.

One approach that has been suggested to avoid this problem is the use of an implant having an outer envelope which comprises a microtextured surface. The aim of providing such a service is to disrupt the capsular architecture and cause ingrowth of the tissue into the microtextured surface, which results in a thinner tissue capsule and lessens the risk of problems due to capsule contracture.

One such device, shown in U.S. Pat. No. 4,955,909, provides a textured surface on the implant from a tetrafluoroethylene (Teflon) that is fabricated in a net-like, three-dimensional grid structure.

Another approach is discussed in the article "Ion-Beam Microtexturing of Biomaterials", *Medical Device and Diagnostic Industry*, volume 6, number 4, Apr. 1984 which describes the use of ion-beam milling of a soft tissue prosthesis to produce microprojections on the surface of the outer envelope and the use of such implants to reduce capsule contracture.

Still another approach is suggested in U.S. Pat. No. 4,955,907, particularly the use of expanded polytetrafluoroethylene filaments which are attached to a stretch fabric backing in a loose weave configuration. Alternatively, silicone molded in geometric patterns may be employed to present the textured surface.

Another approach is discussed in U.S. Pat. No. 4,960,425, wherein a surgical prosthesis having a textured exterior surface formed of non-absorbent material free of pores and interstices is shown. The implant disclosed in this patent is made by molding a silicone envelope over a textured or porous mandrel with either hot or cold compression platens, which are said to create minute indentations, deformations and/or raised portions on the surface of the envelope having a width from 0.0003 to 0.10 inches and a depth from 0.0003 to 0.030 inches, such that the general appearance of the prosthesis is that of an opaque surface, slightly roughened at the touch.

Another approach, and one which is particularly preferred, is taken by U.S. Pat. No. 4,965,430, assigned to the instant assignee. This method prepares a three-dimensional mandrel by laser-drilling an array of blind holes in the surface of the mandrel, used for preparing a mould for a silicone envelope having an arrray of micropillars corresponding to the pattern of blind holes.

Still another device having a micro-textured surface is shown in U.S. Pat. No. 5,002,572, which discloses a mass transfer device having a fluid diffusing or transmitting surface in contact with the soft tissue, the tissue contacting surface being textured to provide a regular pattern of micropillars at least 100 microns in height with dimensions and interpillar spacing each no greater than 5000 microns.

A different approach to the above methods of avoiding capsule contracture is shown in U.S. Pat. No. 4,531,244, specifically, a mammary prosthesis having a plurality of firm protuberances covering the outer surface of the envelope is said to result in flow spaces so that, when the scar capsule contracts and compresses the protuberances, the mammary prosthesis has a spacer for displacement and remains soft. The patent further states that the protuberances, which have a specified height of between 1000–10,000 microns and a diameter between 1000–10,000 microns. This macrotextured surface is further said to provide greater localized pressure in pounds per square inch against the scar capsule in order to maintain a space for implant displacement.

In addition to the attention given above to valve location and tissue capsule contracture concerns, there have been numerous attempts to provide volume-adjustable, anatomically-shaped mammary implants, including tissue-expander devices. Accordingly, various valve and fill-tube designs have been proposed.

One approach has been to situate an injection valve and reservoir at a location remote from the prosthetic implant, the valve being coupled with a fill-tube feeding into a volume-adjustable lumen. Such arrangements are shown in U.S. Pat. Nos. 4,773,908; 4,643,733; and 4,944,749, and further embodied in various products sold by the Mentor Corporation, Goleta, Calif., as the "Becker Expander/Mammary Prosthesis". Once the prosthesis has been filled to the desired level, the remote valve, along with the fill-tube which links the valve to a fill port in the envelope, is uncoupled from the filling port and, once surgically removed, is not intended to be reconnected.

Another volume-adjustable prosthesis having self-contained injection valves is shown in U.S. Pat. No. 4,433,440. A pair of valves are joined with the outer envelope at a common area, unlike than the remotely located Becker valve. One of the valves leads directly into an inner lumen which is joined to the outer envelope, while the other valve leads directly into the outer lumen which surrounds the inner lumen. A difficulty in this type of device is that differential protrusion/expansion of the prosthesis cannot occur other than at the area where both of the valves are commonly joined with the outer envelope, versus areas remote from the valve site.

Accordingly there is still a need for a volume-adjustable prosthesis, particularly a mammary implant which is capable of assuming a variety of anatomical shapes. Further, there is a need for providing an integral valve to allow such a volume-adjustable implant to be filled to a desired level by a physician without post-operative surgical intervention, particularly by means of an external valve-location means that accurately determines the position of the valve. Still further, there is a need to provide a volume-adjustable prosthesis, particularly a mammary implant, which resists problems due to capsule contracture.

SUMMARY OF THE INVENTION

According to the invention, there is provided an implantable prosthetic device inflatable by a self-contained resealable valve. The prosthesis comprises a first flexible elastomeric envelope and a second elastomeric envelope joined with the first envelope along a common surface, respectively defining first and second closed compartments. A resealable injection valve is attached to a selected area of the first envelope, the second envelope being tethered to the valve through the first compartment and spaced from the selected area by a fill-tube for directly inflating the second compartment.

The accompanying Drawings, which are incorporated in and constitute a part of this Specification, illustrate the preferred embodiments of the invention and, together with the Description, serve to explain the principles of the invention.

BRIEF DESCRIPTION OF THE DRAWINGS

FIG. 2 is a perspective view of the remote locator, according to the invention;

FIG. 3 is a top view of the prosthesis and locator combination according to the invention, showing the sensors of the locator orientated with one another to signify a true position of the valve;

FIG. 8 is an enlarged sectional view of an alternative injectable valve assembly of the present invention; and FIG. 9 shows a stacked tissue expander having a pair of valves each with magnetic indicia, one of the valves being tethered for adjusting the volume of a first lumen and the other valve leading into a stacked lumen, according to another embodiment of the invention.

DETAILED DESCRIPTION

References will now be made in detail to several embodiments of the invention, examples of which are illustrated in the accompanying Drawings.

Figure 1:
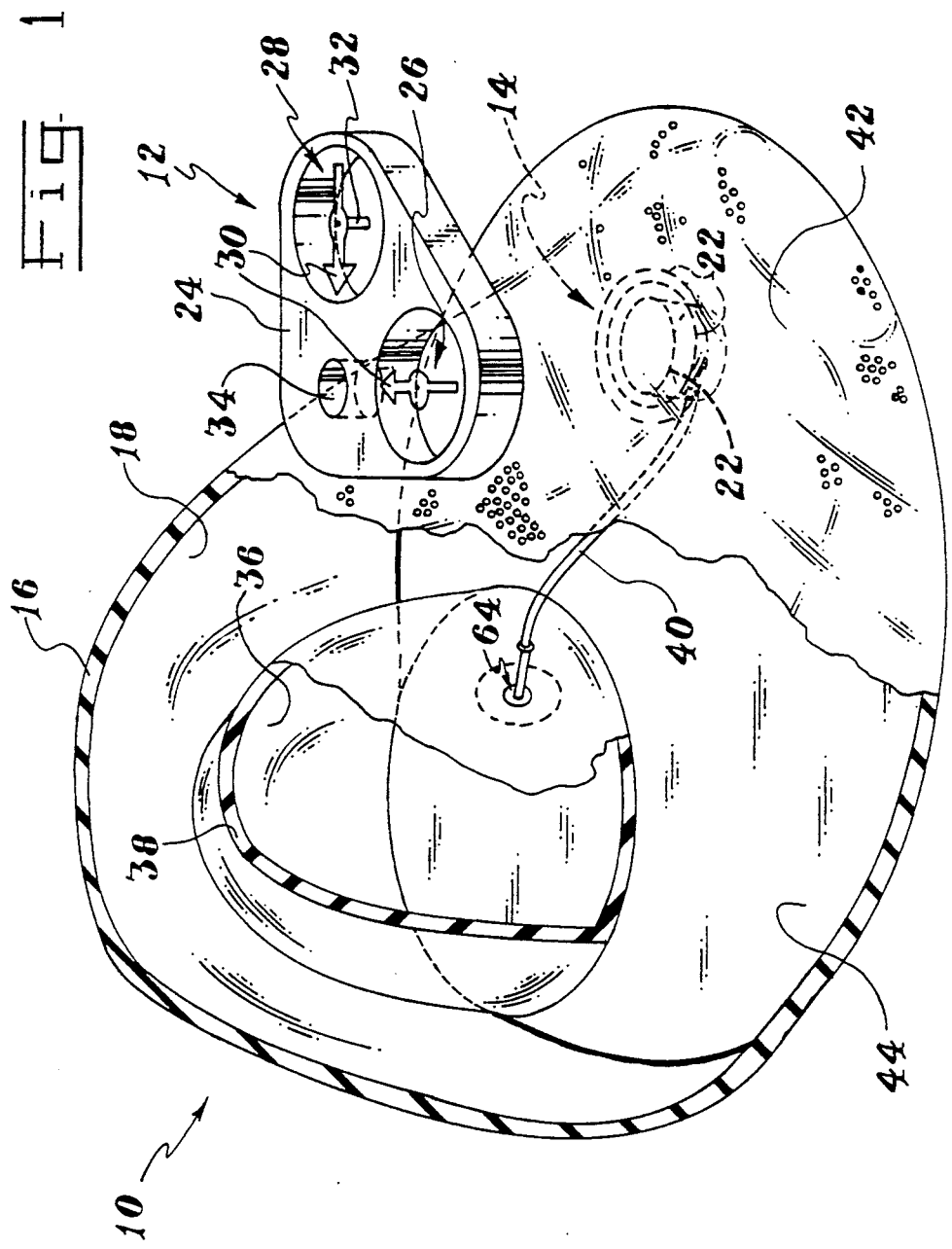
FIG. 1 is a perspective view, partially cut away, of a prosthesis with an inflation valve and a remote magnetic locator, according to one embodiment of the invention, and wherein the injection valve is tethered by a fill-tube to a volume-adjustable lumen of the prosthesis.

A preferred embodiment of the inflatable prosthesis and valve locator combination is shown in FIGS. 1-3. The combination comprises a prosthesis, generally shown at 10, and a locator, generally shown at 12. The implantable prosthetic device 10 comprises an inflation valve, generally indicated at 14 (See also FIGS. 4–5, 7A, 7B, 8 and 9) which is designed to operate with the external locator 12, allowing a surgeon to determine the position of the valve for successive post-operative injections to fill the prosthesis 10 to a desired volume. The prosthesis 10 comprises an outer flexible envelope 16 defining a closed outer lumen 18. The valve is provided with indicia in the form of magnetically-responsive elements, such as the magnets 20 shown in FIGS. 4, 5 and 7B, although other metallic elements could be used provided they are magnetically-responsive. The magnets 20 are preferably coated with a vapor-deposited polymer barrier, of the type generally known in the art, to guard against metal ion release from the magnet. Although it is preferred that magnetics be used, it is understood that a person skilled in the art will appreciate that other means could be used to signify the position of the valve, which are capable of being determined by external locator devices of the type generally described in this Specification. The valve has a generally circular cross section and is preferably joined to an area of the outer envelope which can vary in diameter, shown by the concentric phantom lines 22, as will be appreciated below.

The locator 12 comprises a base 24, including a plurality of sensors 26, 28, each of which preferably comprise a magnetic compass needle 30. The needle 30 is allowed to freely orientate with either the north or south magnetic pole within a closed recess in the base 24. The needle may either be rotatably mounted on the end of a pin 32 or may be free-floating in a fluid that is sealed within the recess (not shown). It will be further understood by those skilled in the art that metallic elements could be provided in the sensor 26 or 28 which would be responsive to a magnetic element 20 in the valve assembly 14. It is important however, that the plurality, in this case the pair of sensors 26 28 be spaced from one another such that when the locator 12 is manuevered into position over the valve 14 the pair of north or south indicating needles 30 orientate with one another and define a third point, shown by the target opening 34 which indicates a true position of the valve 14. In this regard, the magnetic indicating system is somewhat similar to the "triangulating" approach used in navigation, however, this principle has been adapted specifically for use in a device for precisely locating the injection valve of a prosthesis, such as the preferred embodiment of a mammary prosthesis shown in FIGS. 1, 4, 7A–7B and 9. It is preferred that both needles have the same magnetic pole orientation, for example, either both north or both south indicating magnetic elements, so that the heads of both point in the same direction, i.e., the target circle 34. Of course, the needles actually move independently of one another and it is the intersection of their respective axes that defines the target when accurately aligned. It would be further appreciated by those skilled in the art that three or more needles could alternatively be used in a triangular base with a center target (not shown) located at the centroid of the triangle defined by vertices corresponding to each magnetic needle. FIG. 2 shows the needle 30 in a non-orientated position, while FIG. 3 shows the needles pointing toward the target 34 to signify the true location of the underlying valve 14.

Thus, a physician (or nurse) is able to precisely locate the injection valve in successive office visits of the patient, without further surgical intervention needed other than to remove a tissue expander in exchange for a long-dwelling implant.

An advantage of the invention is that the locator actually guides the user (physician or nurse) to the valve site by signifying the proximity and direction of approach of the valve by the user. This is in distinct contrast to the pivoting-types of stud-finders shown, for example, in the above U.S. Pat. No. 3,845,384, which do not guide the user toward the valve location but rather require multiple passes over the site to ascertain the proper coordinates.

Figure 7A:
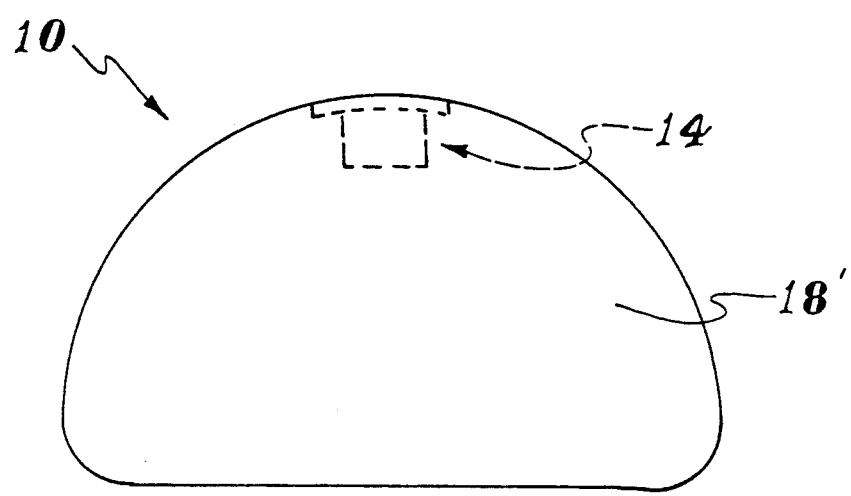
FIG. 7A shows a tissue expander having a rounded shape with a valve of the type used in combination with the locator of the present invention.
Figure 7B:
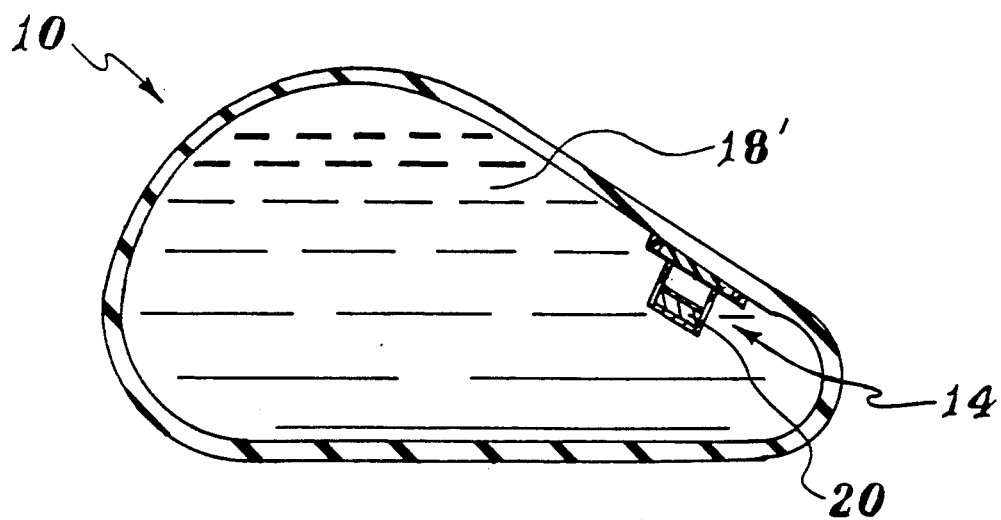
FIG. 7B shows an asymmetric or differential tissue expander having a self-contained valve, according to one preferred embodiment the present invention.

As shown in FIGS. 1, 4 and 7A–7B, the prosthesis 10 may assume a variety of three-dimensional shapes, which are adapted to the specific needs of the patient. For example, FIG. 1 shows a pendulous or ptotic shape, as do FIGS. 4 and 7B, while FIG. 7A shows a rounder shape.

In another embodiment of the invention, it is an object to provide an implant which, when inflated, will assume an asymmetrical shape as described immediately above, thus meeting the needs of particular patients. It has been known to provide an implantable tissue expander (either long-dwelling or short-term) or other prosthesis of a dual-lumen construction. However, such constructions have conventionally been designed so that the inner and outer envelopes of the respective lumens are joined together at an area where the valve is located. Thus, differential tissue expansion is restricted to the area of the outer envelope immediately surrounding the valve. In contrast, it is an object of the present invention to provide tissue expansion at an area remote from the valve in achieving a preferably asymmetrical or pendulous shape, as will be described below.

Figure 4:
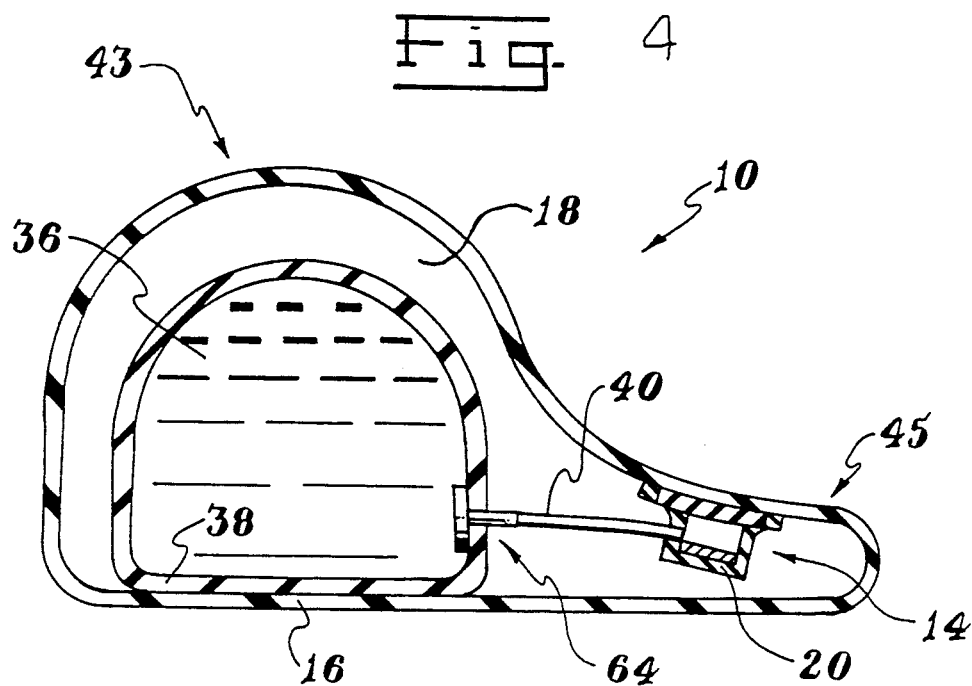
FIG. 4 is a sectional view, taken along the lines 4—4 of FIG. 3.

Another preferred embodiment of a mammary implant 10 is shown in FIGS. 1, 3, 4 and 9. Particularly, in FIGS. 1, 3 and 4, the prosthesis 10 further comprises a nested multi-compartmental arrangement, unlike the embodiments shown in FIGS. 7A–B, which comprise a single lumen, and FIG. 9, which is a stacked multi-compartmental design. Rather than the single lumen 18' shown in FIGS. 7A–7B, the dual lumen embodiment as shown in FIGS. 1, 3, 4 and 9, comprises an outer lumen 18 which is defined by the outer envelope 16 and an inner closed lumen 36 which is defined by the inner envelope 38, shown partially broken-away in FIG. 1. The injection valve 14 and inner lumen 36 are tethered by a fill-tube 40, shown also in FIGS. 3–6 and 9, whereby fluid injected into the valve 14 flows through the fill-tube directly into and inflates the inner lumen 36, without inflating the outer lumen 18. Therefore, the prosthesis 10 shown in FIGS. 1, 3 and 4, is inflatable post-operatively only in the region occupied by the inner lumen 36.

During, manufacture, the outer lumen 18 is permanently filled with silicone gel to a desired level through a conventional silicone elastomer patch which is then sealed. It is preferable to fix the position of the inner lumen 36 by adhering the inner envelope 38 to the outer envelope 16 in a desired area, as shown by FIGS. 1 and 4, using a conventional medical grade silicone elastomer composition.

The prosthesis 10 in one of its embodiments has a ptotic shape (FIGS. 1, 3–4, 7B and 9) with a rounded anterior surface 42 (FIG. 3), which is intended to protrude anteriorly following implantation, and a flattened posterior surface 44 (FIG. 1), lying flat against the tissue. Moreover, it is desirable to fill the inner lumen with saline postoperatively from the upper or rounded surface 42 of the prosthesis which is accessible to injection by the surgeon. It will be understood that gel/saline, gel/gel, saline/saline or other combinations of biocompatible fluids could be used to fill the various lumens of the implant, depending on the desires of the physician. As the inner lumen 36 of the implant 10 is filled with saline (preferably) upon progressive injections of fluid through the valve 14, the volume of the inner lumen 36 is increased as represented by the various positions of the inner envelope 38, shown in phantom in FIG. 3. Such a volume increase results in an increased projection of the inferior portion 43 while maintaining minimal projection of the superior portion 45 of the anterior surface 42.

With respect to implantation of a percutaneous tissue expander, a preferred surgical technique is set forth in "Tissue Expansion-Guidelines Case Analysis", by Gordon H. Sasaki, M.D., dated 1985 and published by Dow Corning Wright Corp., Arlington, Tenn., the entire disclosure of which is hereby incorporated by reference and relied-upon. It is important that certain details be observed for the sake of safety and efficacy in implanting the device described herein. Namely, the surgeon should select an incision size and location which allows for creation of a well-defined, dry pocket; allow for insertion of the implant without distortion; and allow for ready digital access to the pocket to ensure flat implant placement and smoothing of the implant surface. The pocket size created by the surgeon should be of sufficient size to allow the implant to lie flat in the pocket. The measures will reduce the wrinkling of the implant surface. As mentioned above, the inflation valve must be placed to ensure that the injection port is readily locatable, and secure in its pocket. With respect to wrinkling, it is important that, when the tissue expander is inserted, the expander envelope is initially flaccid, i.e., redundant and folded. Injection of saline into the tissue expander to the limits of tissue tolerance is recommended following insertion to minimize the wrinkling and folding of the expander envelope. Once the tissue expander is in its pocket, it should be smoothed out to minimize fold formation. An advantage of the externally-locatable inflation valve of the invention is that, if the projecting fold produces ischemia or thinning of overlying tissue during the expansion process, the tissue expander can be partially deflated for two to three weeks without surgical intervention, allowing tissue stabilization. Periodic expansion may then be resumed. If a projecting fold remains a problem, the implant should be deflated and an attempt made to manipulate the fold to another area. If these attempts are still unsuccessful and buckling of the expander envelope remains a problem, the implant should be removed.

Folds in the tissue expander may also result in weakening and/or deflation of the unit through abrasive micro-motion of the envelope against itself. Tissue expanders left under-inflated for a long period of time or folded envelopes under pressure have developed leaks at the folds resulting in deflation of the unit. Care must also be taken to avoid inadvertent post-operative perforation of the tissue expander during inflation. The location and orientation of the inflation valve should always be confirmed prior to inflation. The inflation needle should always be inserted in the center of the injection port generally perpendicular to the face of the valve (see FIG. 5). Overly acute angles of insertion should be avoided. Moreover, care should be taken so that the envelope does not overlap the valve as this could result in perforation of the envelope during inflation.

The self-contained valve of the present invention, versus the remote valve arrangements used in the prior art tissue expanders, for example the "Becker" products, has the advantage of requiring no distant site for valve placement, thus minimizing the time and trauma for placement and removal of the tissue expander. Also the inherent design of the self-contained valve reduces tube kinking or disconnection. However, as mentioned above, care must be taken to avoid inadvertent puncture of the envelope of the expander. With regard to implantation at the time of surgery the base dimensions of the selected expander may be outlined on the patient using as a guide an appropriate template. A pocket 1 cm larger than the expander will allow the expander to lie flat and helps to prevent buckling of the implant which could lead to an extrusion during expansion.

Particularly in older patients, an anatomicaly-shaped, pendulous expander device should typically be selected for expansion. The tear-drop shape with the integral valve, allows for a broad base and greater projection at the lower half of the expander which, in turn, allows for significant portion of expansion to occur at and below the infra mammary line. Thus, it will be apparent to those skilled in the art that there has been described herein a preferred method of using the subject tissue-expander device.

The particular structure of the integral inflation valve 14 will now be discussed. Referring to FIGS. 4, 5, 7B and 8, the valve 14 comprises a soft ring 46, a self-sealing sheet of silicone material 48 joined to a silicone valve case 50 and a metal cup 52, defining a reservoir 54. The magnet 20 is encased in the cup 52 and has a needle stop 56 overlying the magnet. The soft ring 46 and self-sealing material 48 are joined to the outer envelope 16 by a silicone medical grade adhesive, by simultaneous curing, or other suitable for joining the materials permanently together. FIG. 8 shows the attachment of valve 14 to envelope 16 by means of a layer 57 of medical grade elastomer. It should be noted that the valve assembly 14 is on the internal surface of the outer envelope 16 and, thus, is situated within the outer lumen 18 such that the valve 14 does not protrude above the outwardly surface of the outer envelope 16. The fill-tube 40 penetrates the case 50 and the cup 52 and is in fluid communication with the reservoir 54. Fluid enters the reservoir 54 through the injection needle 58, shown in FIG. 5, and flows from the reservoir 54 through the fill-tube 40 in the direction of arrow 60 toward the inner lumen, as can be appreciated from FIG. 4.

Referring to FIG. 8, there is shown an alternative arrangement of the soft ring 46 in terms of its attachment to the outer envelope 16. Specifically, ring 46 is of a one-piece construction with downwardly projecting flanges 62 that are unsecured to the outer envelope 16. The purpose of the ring 46, and particularly the flanges 62 is to make the valve assembly less externally palpable during use of the implant 10.

Figure 6:
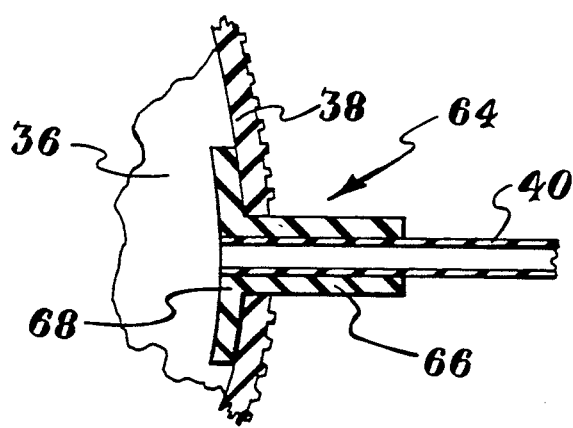
FIG. 6 shows the connection of the tethered fill-tube leading into the inner lumen from the valve reservoir, according to one embodiment of the invention.

Referring to FIG. 6, the fill-tube 40 passes through a port, generally indicated at 64 (also shown in FIGS. 1, 3, 4 and 9) which leads into the inner lumen 36. The fill-tube 40 passes through a sleeve 66 that is integral with a base 68 which forms a T-shape connector. The base 68 is adhered to the internal surface of the inner envelope 38 by means of a suitable medical grade silicone elastomer material. Both the fill-tube 40 and sleeve 66 are preferably made of a silicone tubing material.

Referring to FIG. 9, there is shown a prosthesis 10 having a stacked design wherein a first envelope 70 is joined to a smaller second envelope 72 in a selected area to provide localized or areolar expansion. The first envelope defines a closed first compartment 74 and the second envelope 72 defines a second closed compartment 76. The second compartment 76 is situated on the inferior portion 43 of the anteriorly-projecting surface 42 of the first envelope 70 so as to impart an asymmetrical shape to the prosthesis 10. The first compartment 74 is supplied by a self-contained valve 78 which is tethered by a fill-tube 80 to the first compartment 74. The fill tube 80 extends between a reservoir in the valve 78 and an inlet port 82, such that fluid injected into the valve 78 flows through the tube 80 directly into the first compartment 74, expanding its volume. The volume of the relativley smaller second compartment 76 may also be adjusted by means of the self-contained valve 84 which is spaced from the valve 78, that is, injection of fluid into the valve 84 flows directly into the second compartment 76, thus the valve 84 is not tethered, as is the valve 78. It is possible to distinguish the spaced valves 78 and 84 from one another by using magnets of differing orientations in each. For example, the valve 78 may have a north pole-facing outward magnet, while the valve 84 can have a south pole-facing outward magnet. Accordingly, separate locators (not shown) may be used for each of the valves, for example, the compass needles on one of the locators can indicate the north pole, while the compass needles in another locator can indicate a south-pole. Alternatively the same locator can be used with dual-arrow needles (not shown) which point with arrows of one color to one valve and with arrows of another color to the other valve. This allows for a multi-compartmental stacked adjustable implant to be used without remote valves. An advantage of this particular arrangement is that a large second compartment 74 may be used, since the first compartment need not be punctured for inflation.

An advantage of the long-dwelling tissue expander device according to this invention is that the breast size may be changed as the patient gains or loses weight, further a pendulous shape may be obtained which more closely resembles a natural breast, particularly in larger and/or older patients. In contrasts, the long-dwelling tissue expanders of the prior art, for example, the "Becker Tissue Expander" cannot be inflated once the fill-tube is pulled out of the lumen with the remote valve.

Figure 5:
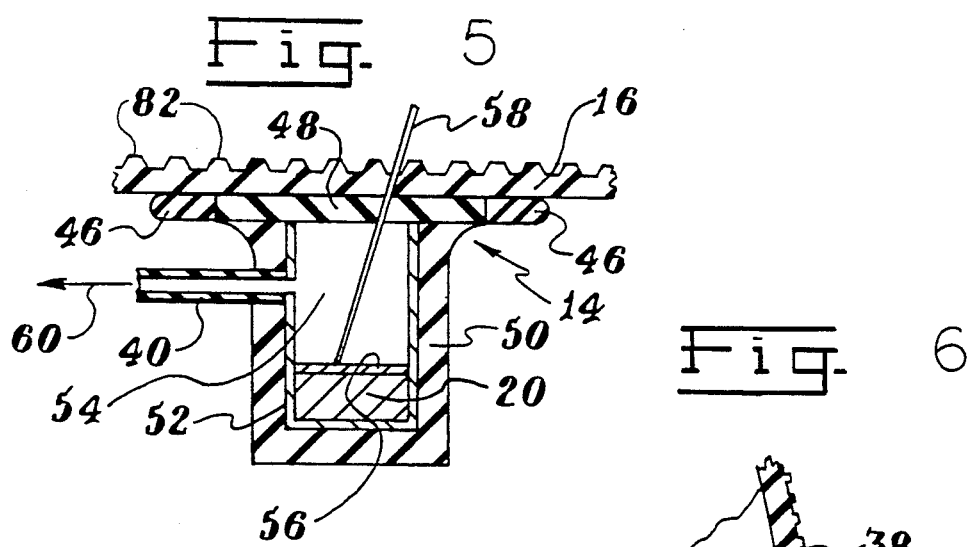
FIG. 5 is a sectional view of the self-sealing injection valve and reservoir, showing the self-sealing valve preferably containing a magnet and being punctured by an injection needle.

Another feature which can be used with any or all of the embodiments of the invention shown herein, is an outer envelope 16 having a micro-textured surface, as shown in FIG. 5. The micro-textured surface is formed by dipping a textured mandrel into a bath of silicone fluid and curing the silicone fluid under pressure then stripping the finished envelope from the mandrel. A preferred method of fabricating the mandrel is disclosed in U.S. Pat. No. 4,965,430 to Curtis, assigned to the assignee of the present invention, the entire disclosure which is hereby incorporated by reference and relied upon. Likewise a preferred method of preparing an envelope having a micro-textured surface in accordance with the present invention, using the mandrel fabricated in accordance with the above U.S. Pat. No. 4,965,430 is disclosed in pending U.S. Pat. application Ser. No. 402,746, filed Sep. 4, 1989 in the name of James M. Curtis, assigned to the assignee of the present invention, the entire disclosure of which is hereby incorporated by reference and relied upon. The tissue-contacting surface of the outer envelope 16 is micro-textured with a pattern of micropillars 82, as shown in FIG. 5, which disrupt the architecture of the fibrous tissue capsule formed around the implant. As a result, the tissue capsule is much thinner and the incidence of clinical capsule contracture problems is significantly reduced. The micropillars 82 have a generally frusto-conical shape such that the diameter of the appex is less than the diameter of the base where the micropillar joins the substrate of the envelope 16. The preferred structure of the micropillars 82 is discussed in detail in the above U.S. Ser. No. 402,746. Several advantages result from the structure of the micropillars 82, including the ease in stripping of a tissue expander from the body prior to insertion of a long-dwelling implant. Further, the frusto-conical shape is believed to reduce irritation of the tissue capsule which can result in microbleeding, as is the case with certain prior art textured implants, discussed above, which have conical, pointed projections. As a result, the surgeon has significantly less difficulty with the tissue capsule after removing the expander to prepare for implanting the long-dwelling prosthesis.

While the invention has been described with respect to certain embodiments, it will be obvious that various modifications may be contemplated by those skilled in the art without departing from the scope of the invention as hereafter defined by the following claims.

What is claimed is:

1. An implantable prosthetic device inflatable by a self-contained resealable valve comprising:
    a outer flexible elastomeric envelope;
    an inner elastomeric envelope spaced inwardly from the outer envelope, respectively defining an outer closed lumen and an inner closed lumen nested within the outer lumen;
    a resealable injection valve attached to a selected area of the outer envelope, the inner envelope being tethered to the valve and spaced inwardly from the selected area by a fill-tube for directly inflating the inner lumen.

2. An implantable prosthetic device inflatable by a self-contained resealable valve comprising:
    a first flexible elastomeric envelope;
    an second elastomeric envelope joined with the first envelope along a common surface, respectively defining first and second closed compartments;
    a resealable injection valve attached to a selected area of the first envelope, the second envelope being tethered to the valve through the first compartment and spaced from the selected area by a fill-tube for directly inflating the second compartment.

* * * * *